United States Patent [19]
Cane et al.

[11] Patent Number: 5,239,984
[45] Date of Patent: Aug. 31, 1993

[54] HAND-HELD OPTO-DIAGNOSTIC INSTRUMENT SYSTEM

[76] Inventors: Richard M. Cane, 6141 Miramar Pkwy.; Wayne R. Byard, 6142 Miramar Pkwy., both of Miramar, Fla. 33023

[21] Appl. No.: 797,724

[22] Filed: Nov. 25, 1991

[51] Int. Cl.⁵ .................................................. A61B 1/22
[52] U.S. Cl. ............................................... 128/9; 128/6
[58] Field of Search ....................... 128/9, 23, 3, 7, 8, 128/4, 6; 358/98

[56] References Cited

U.S. PATENT DOCUMENTS

| | | | |
|---|---|---|---|
| 3,638,643 | 2/1972 | Hotchkiss | 128/9 |
| 4,012,686 | 3/1977 | Heine | 128/23 X |
| 4,517,963 | 5/1985 | Michel | 128/6 |
| 4,565,423 | 1/1986 | Ueda | 128/6 |
| 4,651,202 | 3/1987 | Arakawa | 128/4 X |
| 4,712,537 | 12/1987 | Pender | 128/9 |
| 4,979,498 | 12/1990 | Oneda et al. | 128/23 X |

Primary Examiner—Stephen R. Crow
Assistant Examiner—Karen A. Jalbert
Attorney, Agent, or Firm—M. K. Silverman

[57] ABSTRACT

There is provided a video monitoring, recording and transmission elements for use in combination with a hand-held medical opto-diagnostic office-use instrument such as an otoscope and an ophthalmoscope. The adaptor, beam splitter and video camera head portions of the system are proportioned in physical size to about the same size as an existing hand-held, office-use, examination instrument of the physician. The components of the system may be selectably coupled and de-coupled with an otherwise conventional otoscope or ophthalmoscope.

5 Claims, 2 Drawing Sheets

HAND-HELD OPTO-DIAGNOSTIC INSTRUMENT SYSTEM

BACKGROUND OF THE INVENTION

Various hand-held instruments for use by a physician during office examination of a patient have been known in the art for many years. Such hand-held instruments include the otoscope (for examination of the ear and throat) and ophthalmoscope (for examination of the eye).

Also, in the prior art, it has been known to employ miniature or micro video cameras in connection with various surgical procedures which occur in the operating room. One example of such prior art is U.S. Pat. No. 4,963,903 (1990) entitled Camera Positioning System by Richard M. Cane, one of the within co-inventors. Such video cameras are, technically, known as remote head color CCD cameras. Such cameras employ an array of semi-conductive chips using a technology known as charge coupled diode sensors. Such micro-cameras are capable of yielding more than 500 lines of resolution per axis, resulting from the sue of 400,000 or more pixels in the screen. Use of such micro-video cameras and related equipment, such as endocouplers, have been known of some time in connection with certain types of surgery and, particularly, surgery conducted through the use of a small incision in the body wall in a procedure which is know as a videoendoscopy. Such procedures have become increasingly commonplace in connection with procedures upon the gall bladder, appendix, intestine, and reproductive organs where the problem is of an internal nature.

Despite the relatively widespread use of micro-video technology in the operating room, which includes the display of a procedure upon both local and remote monitors, the benefits of this technology have not, heretofore, manifested themselves in the physician's office within the context of otherwise routine examination and diagnosis.

The need for, and benefit of, the expression of this technology into an office examination environment is evident in many area. In the first instance, the patient and doctor might both observe, upon a local monitor, a greatly enlarged subject of the examination. A video record of such examination may be kept, and the patient and doctor, and/or consultants, may be provided with either the video of selected positive print frames of a video tape of the examination.

Enhanced light may be furnished to the site of observation, and extra battery-power or A/C power may be provided to the doctor's hand-held instrument. Also, in a more exotic context, a video link to a satellite or other transmission means may be provided from a video interface of the system such that consultants may be utilized either in real time, or in a batch mode, to provide "second opinions" to the examining physician who may be located in a geographically remote region and/or may possess limited skills in the specialty to which the examination relates.

The instant invention may be thereby understood as an enhancement of the power and utility of conventional hand-held, in-office medical diagnostic instruments in the nature of the otoscope and ophthalmoscope.

SUMMARY OF THE INVENTION

The invention relates to a system for use in combination with a hand-held medical opto-diagnostic instrument for in-office physician use. Through the use of a suitable adaptor, a beam splitter is opto-mechanically interfaced with the optical input to the opto-diagnostic instrument. One output of the beam splitter is optically interfaced to a video camera head and the other output of the beam splitter is interfaced to the eyepiece of the instant system. The output of the video camera head is connected to the input of a micro-video camera which, in turn, is connected to the input of a video monitor in a position viewable by at least the physician and, optionally, the patient as well. There may be provided an alternative or augmentive light source, through an optic fiber cable connection o the optical input of the opto-diagnostic hand-held instrument. There may also, be provided a radio link output from the micro-video camera, for remote transmission.

The opto-diagnostic office use system may take a variety of forms including, without limitation, use with an otoscope and ophthalmoscope.

It is, accordingly an object of the present invention to provide a means for observing by both doctor and patient either simultaneously or in time-delayed fashion, an enlarged image of the subject of a physician's examination with a hand-held opto-diagnostic instrument.

It is another object of the invention to provide a means for storage and later examination of the medical subject of an examination by a hand-held opto-diagnostic instrument.

It is a further object of the present invention to provide a means by which the object of such examination may be radio-linked to other physicians.

It is a yet further object of the invention to provide a system of the above type to furnish to the examining doctor enhanced illumination, extended battery capability, and the means to explain, both concurrently with the following the examination, his findings with the patient and other parties.

The above and yet other objects and advantages of the invention will become apparent from the hereinafter set forth Brief Description of the Drawings, Detailed Description of the Invention, and Claims appended herewith.

DETAILED DESCRIPTION OF THE INVENTION

Figure 1:
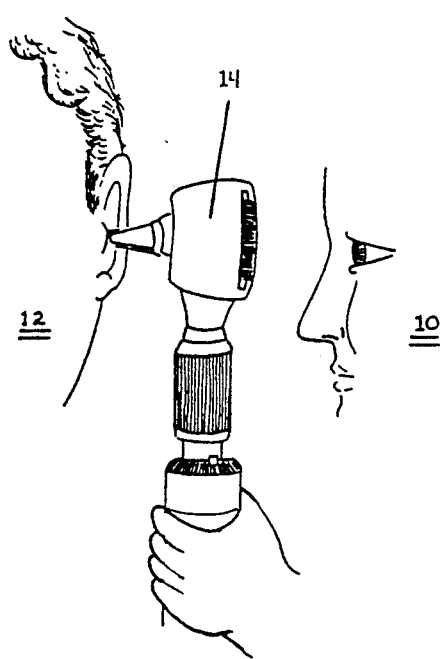
FIG. 1 is a conceptual view showing usage by a physician of a prior art otoscope.

With reference to FIG. 1, there is shown the manner in which a physician 10 may, in the course of an office visit by a patient 12, examine the patient through the use of a conventional hand-held opto-diagnostic instrument such as an otoscope 14. It is to be understood that the term otoscope is used hereinafter is used in a sense equivalently to the term ophthalmoscope in that, for purposes of the instant invention, the function of these other hand-held diagnostic instruments is equivalent to that of the otoscope.

It is noted that such hand-held opto-diagnostic instruments are glorified versions of magnifying glasses in which there is provided a light source and batteries therefor within the hand-held portion 16 of the instrument. Certain otoscopes and, particularly, ophthalmoscope, are provided with a variety of lamp types, filters, and aperture geometries to achieve one or another desired optical effect. Also, most otoscopes and ophthalmoscopes are provided with a dozen or more different lenses that may be utilized to obtain varying degrees of enlargement, polarization, red-filtering, and aperture cross-hair configuration.

Notwithstanding the existence of such "enhancements" in conventional otoscopes and ophthalmoscopes, there does not, as above noted in eh Background o the Invention, exist any means by which the patient may observe what a doctor is observing and by which a doctor may observe the same on a video monitor screen, much less record and transmit the same to other doctors the visual information derived in the examination of the patient.

Responsive to the above, the instant inventive system provides for the placement of a customized adaptor coupling 18 upon the existing eyepiece 20 of the existing otoscope 14. In other words, the adaptor coupling 18, and those other elements set forth below, constitutes a system which may be selectively added to a physician's otoscope without any permanent change or adaptation, and then removed therefrom. As such, the physician may connect the present system to his existing otoscope on an "as needed" basis where, for example, a particular patient presents a situation which, from either a medical or legal point of view, is out of the ordinary and, therefore, would justify the use of the additional elements associated with the instant system.

Shown to the right of coupling 18 is a beam splitter 22 having an interface portion 24 for optical connection to coupling 18 and an eyepiece portion 26. The beam splitter is an optical device which divides an incoming beam of light into two light outputs, typically through the use of an inclined plane having a partial refractive property such that a portion of the incoming beam of light will be refracted or diverted from its incident direction while an unrefracted portion of the incoming beam will continue along its original path of propagation to the eyepiece of the beam splitter. Beam splitters have been known in the art of optics for over a century. However, a beam splitter suitable for use in the instant invention is one having a focal length of 25 or 35 millimeters and one in which the ratio of light flux permitted to propagate in the direction of input to the ratio of light flux refracted to a secondary direction is thirty-to-seventy.

With further reference to the view of FIG. 2 it is noted that the refracted portion of light input 28 to he beam splitter 22 is directed downward to an image coupler 30 (below described in further detail) which, in turn feeds into a video camera head 32. It is noted that the image coupler may, and often is, integrated into the output of the beam splitter.

Figure 2:
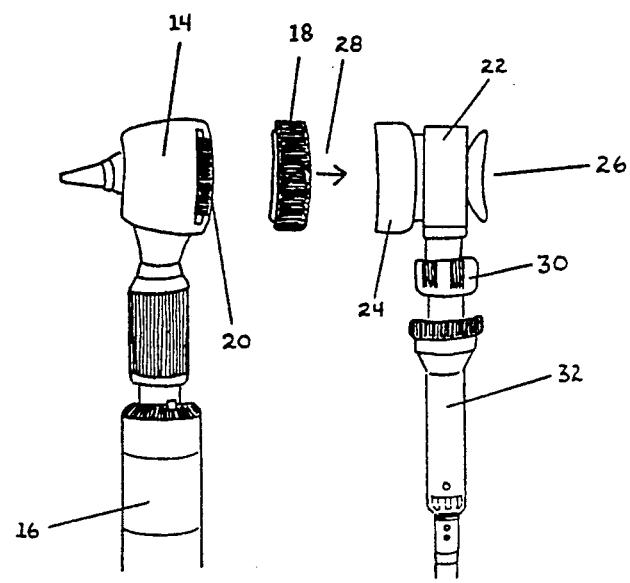
FIG. 2 is an exploded view showing the components of the invention opto-diagnostic system.
Figure 3:
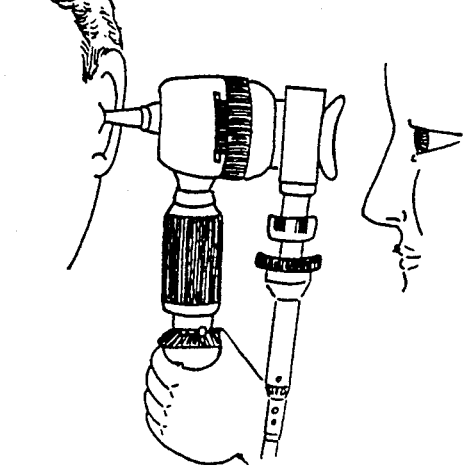
FIG. 3 is an assembled, operational view of the element shown in FIG. 2.

The elements of FIG. 2 are shown in assembled view in FIG. 3. Therefrom, it may be appreciated that the physician may employ the inventive system in substantially the same fashion as the conventional otoscope. Also, the beam splitter 22 and video camera head 32 are, in combination, comparable in size to the conventional otoscope.

Figure 4:
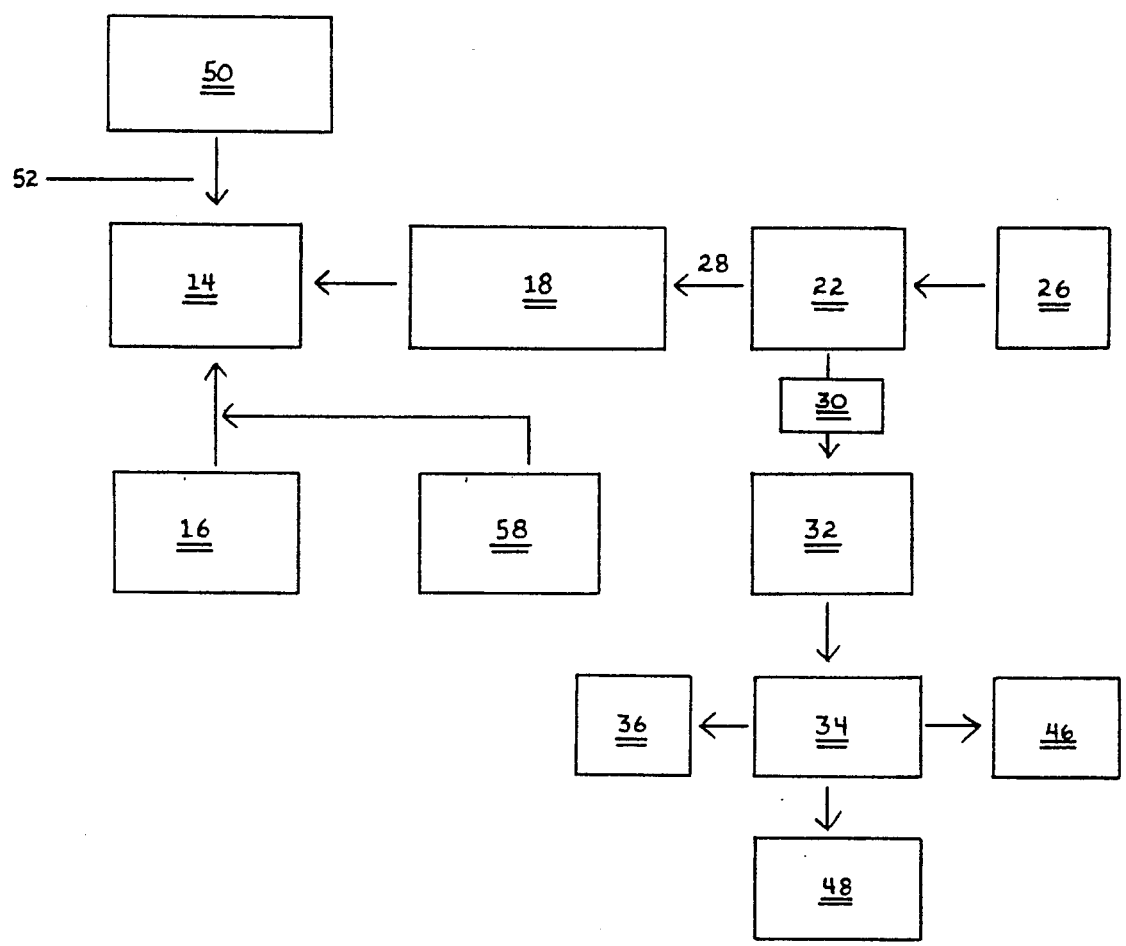
FIG. 4 is a block diagrammatic view of the entire inventive system, including optional components thereof.

With reference to the block diagram view of FIG. 4, it may be seen that the instant system further includes a micro-video camera 34 and a video monitor 36. The micro-video camera will, in a preferred embodiment, comprise a remote head color camera utilizing charge coupled diode optical sensors.

Figure 5:
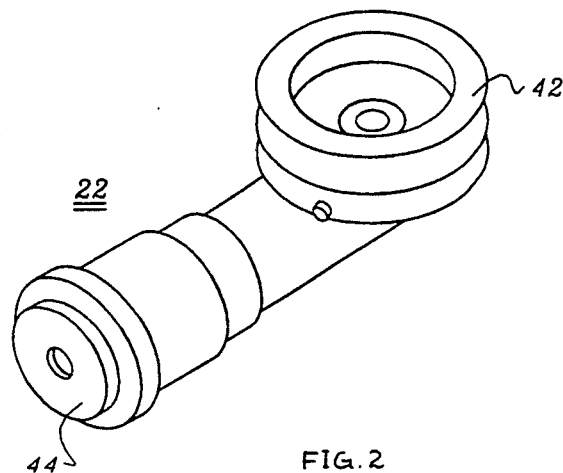
FIG. 5 are perspective views of two types of beam splitter that may be used with the invention.

In FIG. 5 it is noted that the beam splitter input to video camera head 32 will comprise a standard "c" mount 44 of the beam splitter. The beam splitter 22 will in a preferred embodiment be provided with a standard boroscope mount 42 such that is may readily interface with a large variety of endoscopes.

In FIG. 5 is shown one type of commonly available beam splitter 22.

With further reference to FIG. 4, it is noted that the micro video camera 34 may be provided with an interactive communications link 46 which, dependent upon the application, may be either telephone line print-to-print, microwave, or satellite-like in character as, for example, where remote transmission, either in real time or batch format, to a consulting physician is desirable. Such applications will be of particular value to physicians or paramedical personnel in remote or third world locations in which the examining medical personnel often is not a physician of suitable qualification to make a diagnosis. Further, the system may be provided with video recording means 48 such that a record may be kept of every examination in which the inventive system is utilized.

There is further shown in FIG. 4 the capability of the present system to provide more supplemental or alternative lighting sources 50 through the use of a fiber optic cable connection 52 to the otoscope 14. Through the use of such supplemental or alternative light sources, a physician can be saved the inconvenience of changing instruments or changing light bulbs within his otoscope.

Also, as a further option in the instant system there may be provided, intermediately between beam splitter 22 and eyepiece 26, any one of a variety of lenses or aperture selections such that, again, the physician is saved the inconvenience of changing lenses or aperture sizes on the pre-existing hand-held otoscope.

In FIG. 4 there is also shown a supplemental power source 58 which may be provided for usage to power the light source of the otoscope when the present system is in use, thereby minimizing drain from the portable battery source of the conventional otoscope.

In view of the above, it is to be appreciated that there is provided a sophisticated video monitoring, recording and transmission system which, in addition, operates to augment the conventional capabilities of the hand-held diagnostic instrument of the physician so that the objects set forth in the Summary of the Invention are effectively attained.

Accordingly, while there has been shown and described the preferred embodiment of the present invention it is to be appreciated that the invention may be embodied otherwise than is herein specifically shown and described and that within said embodiment certain changes may be made in the form and arrangement of the parts without departing from the underlying idea or principles of this invention within the scope of the Claims appended herewith.

Having thus described our invention what we claim as new, useful and non-obvious and, accordingly, secure by Letters Patent of the Unites States is:

1. A hand-held opto-diagnostic system for use within a conventional physician-patient examining distance not exceeding the manual reach of the doctor, the system comprising:
   (a) a hand-held, non-surgical, opto-diagnostic medical instrument, said instrument including a light source, an eyepiece, a direct view optical pathway for light generated by said light source, and a power supply for said light source;
   (b) a hand-held mechanical and optical adapter proportioned for selectable coupling to, and de-coupling from, said eyepiece of said instrument without modifications of said optical pathway thereof,
   (c) a beam splitter mechanically and optically coupled into said optical pathway to said adapter, said pathway originating from said instrument and extending into said beam splitter, a first optical output of said beam splitter includes said direct view optical pathway of said instrument, said path directed to a system eyepiece located within said conventional physical-patient examining distance thereof, and a second output of said beam splitter includes an optical pathway mechanically and optically coupled to an input to a video camera head coupled to a video camera; and
   (d) video monitoring and recording means opto-electronically coupled to an output of said video camera.

2. The system as recited in claim 1 in which said beam splitter and a video head of said video camera are proportioned in physical size to about the physical size of said opto-diagnostic medical instrument.

3. The system as recited in claim 2, further comprising an informational transmission link electronically connected to an output of said video camera.

4. The system as recited in claim 2, further comprising an alternative light source optically coupled to said instrument.

5. The system as recited in claim 2, further comprising a supplemental power source electrically connected to a battery power circuit of said instrument.

* * * * *